United States Patent [19]

Warriner

[11] Patent Number: Plant 6,463

[45] Date of Patent: Dec. 13, 1988

[54] ROSE PLANT JACPAW

[75] Inventor: William A. Warriner, Tustin, Calif.

[73] Assignee: Jackson & Perkins Co., Medford, Oreg.

[21] Appl. No.: 945,131

[22] Filed: Dec. 22, 1986

[51] Int. Cl.[4] ..... A01H 5/00

[52] U.S. Cl. ..... Plt./11

[58] Field of Search ..... Plt./11

*Primary Examiner*—Robert E. Bagwill

*Attorney, Agent, or Firm*—Majestic, Gallagher, Parsons & Siebert

[57] ABSTRACT

A hybrid tea rose variety having large, high-centered, pink and white flower; pleasant fragrance; long cut flower vase life; profusion of glands and prickles on petioles and peduncles; and dark green foliage combined with vigorous upright growth habit.

1 Drawing Sheet

This present invention relates to a new and distinct variety of rose plant of the hybrid tea class which was originated by crossing the variety Honor, U.S. Plant Pat. No. 4,167, with the variety Love, U.S. Plant Pat. No. 4,437.

The primary objective of this breeding was to produce a new rose variety of the hybrid tea class combining the white color and large flower of Honor with the profuse flowering and excellent habit of Love. This objective was substantially achieved along with other desirable improvements as evidenced by the following unique combination of characteristics which are outstanding in the new variety and which distinguish it from its parents as well as from all other varieties of which I am aware:

1. Large, white and pink, high-centered flower;
2. Strong, upright growth habit;
3. Dark green, leathery foliage;
4. Glandular and prickly peduncle and petiole;
5. Pleasant fragrance; and
6. Long life as a cut flower.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:

*Seed parent.*—Honor, U.S. Plant Pat. No. 4,167.

*Pollen parent.*—Love, U.S. Plant Pat. No. 4,437.

Classification:

*Botanical.*—Rosa hybrid.

*Commercial.*—Hybrid tea.

FLOWER

Observations made from specimens grown in a greenhouse at Irvine, Calif. in September and October, 1986.

Blooming habit: Continuous.

Bud:

*Size.*—1½" when petals start to unfurl.

*Form.*—Long, pointed ovoid.

*Color.*—When sepals first divide, basic color is white (White Group 155D) with each petal edged in pink (Red Group 52C to D); when half blown, upper side of petals, basic color is white (White Group 155D) with edges in pink (Red Group 52C to D); lower side of petals, basic color is white (White Group 155D) with edges in pink (Red Group 52C to D).

*Sepals.*—Color: Green Group 138A with a bronze colored strip down the center of the sepal. Three appendaged sepals normally to heavily appendaged. Two unappendaged sepals hairy edge.

*Receptacle.*—Color: Green Group 138A with some bronze coloration. Shape: Funnel. Size: Large. Surface: Smooth.

*Peduncle.*—Length: Long. Surface: Rough, prickly and glandular. Color: Bronzy. Strength: Stiff, erect.

Open bloom:

*Size.*—Average open size 5".

*Borne.*—Singly.

*Stems.*—Medium, strong.

*Form.*—When first open, high center. Permanence: Flattens, outer petals curl back quill fashion.

*Petalage.*—Number of petals under normal conditions: 35–40.

*Color.*—Center of flower: Upper side of petals, basic color is White Group 155D with the petal edges Red Group 52C to D; reverse side of petals, basic color is White Group 155D with the petal edges Red Group 52C to D. Base of petals, Yellow half moon at the petal base (Yellow Group 2A). Major color: White Group 155D.

*Variegations.*—None.

*Discoloration.*—General tonality at end of first day: None. Third day: None.

*Fragrance.*—Slight to moderate.

Petals:

*Texture.*—Thick.

*Shape.*—Round.

*Form.*—Tips slightly recurved, edges slightly quilled.

*Arrangement.*—Imbricated. Petaloids in center, few.

*Persistence.*—Drop off cleanly.
*Lastingness.*—On the plant, long. As cut flower, very long.

Reproductive parts:
*Anthers.*—Large, many. Color: White. Arrangement: Regular around styles, mixed with a few petaloids.
*Filaments.*—Color: Yellow.
*Pollen.*—Gold yellow.
*Styles.*—Color: Red.
*Stigmas.*—Color: Greenish white.

PLANT

Form: Bush.
Growth: Vigorous, upright.
Foliage:
*Number of leaflets on normal mid-stem leaves.*—5 to 7.
*Size.*—Medium.
*Quantity.*—Normal.
*Color.*—New foliage: Reddish. Old foliage: Dark green.

Leaflets:
*Shape.*—Oval.
*Texture.*—Leathery.
*Edge.*—Serrated.
*Serration.*—Single, small.

*Petiole.*—Rachis: Color: Green. Underside: Rough with prickles and glands.
*Stipules.*—Medium, bearded.
*Disease resistance.*—Susceptible to mildew, under normal growing conditions at Irvine, Calif.

Wood:
*New wood.*—Color: Reddish. Bark: Smooth.
*Old wood.*—Color: Green. Bark: Smooth.

Prickles:
*Quantity.*—On main canes from base: Ordinary. On laterals from main canes: Ordinary.
*Form.*—Hooked downward.
*Color when young.*—Red.

Small prickles:
*Quantity.*—On main stalks, few. On laterals, few.
*Color.*—Brown.

I claim:

1. A new and distinct variety of rose plant of the hybrid tea class, substantially as herein shown and described, characterized particularly as to novelty by the unique combination of its large, high-centered, pink and white flower; pleasant fragrance; long cut flower vase life; profusion of glands and prickles on petioles and peduncles; and its dark green foliage combined with vigorous upright growth habit.

* * * * *

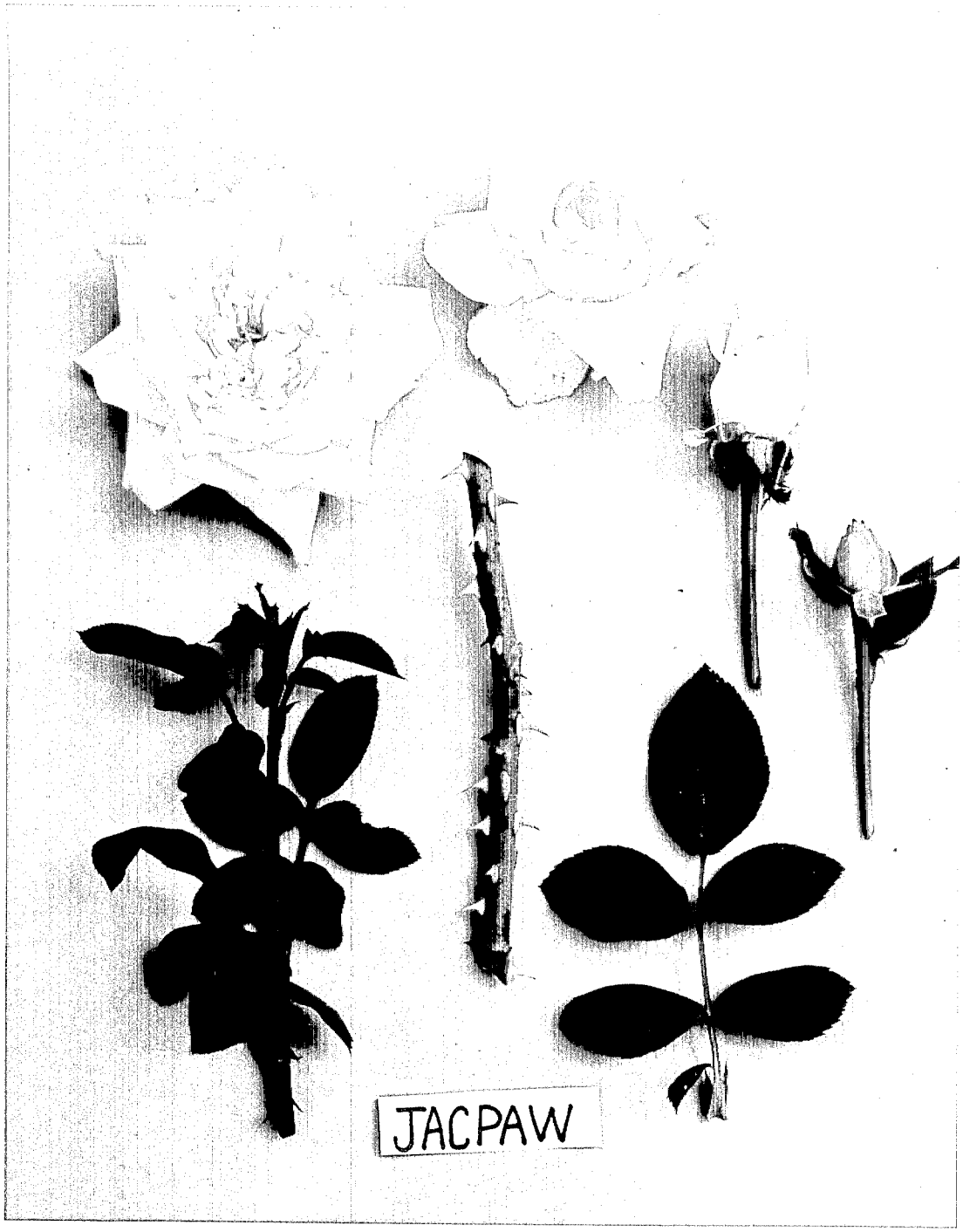
JACPAW